(12) United States Patent
Donovan

(10) Patent No.: US 6,312,708 B1
(45) Date of Patent: *Nov. 6, 2001

(54) BOTULINUM TOXIN IMPLANT

(75) Inventor: Stephen Donovan, Capistrano Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/624,003

(22) Filed: Jul. 21, 2000

Related U.S. Application Data

(63) Continuation-in-part of application No. 09/587,250, filed on Jun. 2, 2000.
(51) Int. Cl.[7] .......................... A61K 39/02; A61K 39/00
(52) U.S. Cl. ....................... 424/423; 424/422; 424/426; 424/184.1; 424/236.1
(58) Field of Search ................................... 424/423, 422, 424/426, 184.1, 236.1

(56) References Cited

U.S. PATENT DOCUMENTS 5,906,826 * 5/1999 Emery et al. ..................... 424/422

FOREIGN PATENT DOCUMENTS

WO 94/15629   7/1994  (WO) .

OTHER PUBLICATIONS

A. Carruthers, et al., Toxins 99, New Information About the Botulinum Neurotoxins; *Dermatol Surg 2000;* 26(3): pp. 174–176.

* cited by examiner

*Primary Examiner*—Thurman K. Page
*Assistant Examiner*—Blessing Fubara
(74) *Attorney, Agent, or Firm*—Martin A. Voet; Robert J. Baran; Carlos A. Fisher

(57) ABSTRACT

A controlled release system for multiphasic, in vivo release of therapeutic amounts of botulinum toxin in a human patient over a prolonged period of time. The controlled release system can comprise a plurality of botulinum toxin incorporating polymeric microspheres.

20 Claims, No Drawings

BOTULINUM TOXIN IMPLANT

CROSS REFERENCE

This application is a continuation in part of Ser. No. 09/587,250, filed Jun. 2, 2000.

BACKGROUND

The present invention relates to an implantable drug delivery system. In particular, the present invention relates to an implantable botulinum toxin delivery system.

A drug implant can deliver a pharmaceutical in vivo at a predetermined rate over a specific time period. Generally, the release rate of a drug from an implant is a function of the physiochemical properties of the implant material and incorporated drug. Typically, an implant is made of an inert material which elicits little or no host response.

An implant can comprise a drug with a biological activity incorporated into a carrier material. The carrier can be a polymer or a bioceramic material. The implant can be injected, inserted or implanted into a selected location of a patient's body and reside therein for a prolonged period during which the drug is released by the implant in a manner and amount which can impart a desired therapeutic efficacy.

Polymeric carrier materials can release drugs due to diffusion, chemical reaction or solvent activation, as well as upon influence by magnetic, ultrasound or temperature change factors. Diffusion can be from a reservoir or matrix. Chemical control can be due to polymer degradation or cleavage of the drug from the polymer. Solvent activation can involve swelling of the polymer or an osmotic effect. See e.g. *Science* 249;1527–1533:1990.

A membrane or reservoir implant depends upon the diffusion of a bioactive agent across a polymer membrane. A matrix implant is comprised of a polymeric matrix in which the bioactive agent is uniformly distributed. Swelling-controlled release systems are usually based on hydrophilic, glassy polymers which undergo swelling in the presence of biological fluids or in the presence of certain environmental stimuli.

Preferably, the implant material used is substantially non-toxic, non-carcinogenic, and non-immunogenic. Suitable implant materials can include polymers such as poly (2-hydroxy ethyl methacrylate) (p-HEMA), poly(N-vinyl pyrrolidone) (p-NVP)+, poly(vinyl alcohol) (PVA), poly (acrylic acid) (PAA), polydimethyl siloxanes (PDMS), ethylene-vinyl acetate copolymers (EVAc), polyvinylpyrrolidone/methylacrylate copolymers, poly (lactic acid) (PLA), poly(glycolic acid) (PGA), polyanhydrides, poly(ortho esters), collagen and cellulosic derivatives and bioceramics, such as hydroxyapatite (HPA), tricalcium phosphate (TCP), and aliminocalcium phosphate (ALCAP). Lactic acid, glycolic acid, collagen and copolymers thereof can be used to make biodegradable implants.

Polymeric implants capable of prolonged delivery of a therapeutic drug are known. For example, a subdermal reservoir implant comprised of a nonbiodegradable polymer can be used to release a contraceptive steroid, such as progestin, in amounts of 25–30 mg/day for up to sixty months (i.e. the Norplant® implant). Additionally, Dextran (molecular weight about 2 million) has been released from implant polymers.

An implant made of a nonbiodegradable polymer has the drawback of requiring both surgical implantation and removal. Hence, biodegradable implants have been used to overcome the evident deficiencies of nonbiodegradable implants. See, e.g., U.S. Pat. Nos. 3,773,919 and 4,767,628. A biodegradable polymer can be a surface eroding polymer, as opposed to a polymer which displays bulk or homogenous degradation. A surface eroding polymer degrades only from its exterior surface, and drug release is therefore proportional to the polymer erosion rate. A suitable such polymer can be a polyanhydride. An implant can be in the form of solid cylindrical implants, pellet microcapsules, or microspheres. Since a biodegradable implant releases drug while degrading there is typically no need to remove the implant. See e.g. *Drug Development and Industrial Pharmacy* 24(12) ;1129–1138:1998. A biodegradable implant can be based upon either a membrane or matrix release of the bioactive substance. Biodegradable microspheres can be implanted by injection through a conventional fine needle or pressed into a disc and implanted as a pellet.

A biodegradable implant preferably retains its structural integrity throughout its desired duration of drug release so that it can be removed if removal is desired or warranted. After the incorporated drug falls below a therapeutic level, a biodegradable implant can degrade completely without retaining any drug which can be released at low levels over a further period. Subdermal implants and injectable microspheres made of biodegradable materials, such as polymers of polylactic acid (PLA), polyglycolic acid (PGA) polylactic acid-glycolic acid copolymers, polycaprolactones and cholesterol are known. Additionally, biodegradable polyanhydride polymer implants are known, and have been used for example as an intracranial implant to treat malignant gliomas with carmustine. Brem, H., et al, Placebo-Controlled Trial of Safety and Efficacy of Intraoperative Controlled Delivery by Biodegradable Polymers of Chemotherapy for Recurrent Gliomas, Lancet 345;1008–1012:1995.

Commercially available PLGA (biodegradable) drug incorporating microspheres include the Lupron Depot® (leuprolide acetate), Enantone Depot®, Decapeptil® and Pariodel LA®. Problems with existing microsphere formulations include low encapsulation efficiency, peptide inactivation during the encapsulation process and difficulties in controlling the release kinetics.

A least three methods for preparing polymeric microspheres, including microspheres composed of a biodegradable polymer, are known. See e.g. *Journal of Controlled Release* 52(3);227–237:1998. Thus, a solid drug preparation can be dispersed into a continuous phase consisting of a biodegradable polymer in an organic solvent or, an aqueous solution of a drug can be emulsified into the polymer-organic phase. Microspheres can then be formed by spray-drying, phase separation or double emulsion techniques.

Hydrogels have been used to construct single pulse and multiple pulse drug delivery implants. A single pulse implant can be osmotically controlled or melting controlled. Doelker E., *Cellulose Derivatives*, Adv Polym Sci 107; 199–265:1993. It is known that multiple pulses of certain substances from an implant can be achieved in response to an environmental change in a parameter such as temperature (*Mater Res Soc Symp Proc,* 331;211–216:1994; *J. Contr Rel* 15;141–152:1991), pH (*Mater Res Soc Symp Proc,* 331;199–204:1994), ionic strength (*React Polym,* 25;1 27–137:1995), magnetic fields (*J. Biomed Mater Res,* 21;1367–1373:1987) or ultrasound.

Protein Implants

Implants for the release of various macromolecules are known. Thus, biocompatible, polymeric pellets which incorporate a high molecular weight protein have been implanted and shown to exhibit continuous release of the protein for periods exceeding 100 days. Additionally, various labile, high molecular weight enzymes (such as alkaline phosphatase, molecular weight 88 kD and catalase, molecular weight 250 kD) have been incorporated into biocompatible, polymeric implants with long term, continuous release characteristics. Generally an increase in the polymer concentration in the casting solution decreases the initial rate at which protein is released from the implant. *Nature* 263; 797–800:1976.

Furthermore, it is known that albumin can be released from an EVAc implant and polylysine can be released from collagen based microspheres. Mallapragada S. K. et al, at page 431 of chapter 27 in Von Recum, A. F. *Handbook of Biomaterials Evaluation,* second edition, Taylor & Francis (1999). Additionally, the release of tetanus toxoid from microspheres has been studied. Ibid at 432. Sintered EVAc copolymer inserted subcutaneously has been shown to release insulin over a period of 100 days. Ibid at 433.

Proteins, such as human growth hormone (hGH) (molecular weight about 26 kD), have been encapsulated within a polymeric matrix which when implanted permits the human growth hormone to be released in vivo over a period of about a week. See e.g. U.S. Pat. No. 5,667,808.

The concept of controlled release antigen delivery systems has been the subject of intensive research efforts. A motivation for this work has been the development of continuous and pulsatile release vaccine delivery systems whereby long lasting protection through immunization can be provided through a single dose system as opposed to multiple, separate dosing vaccine administration schedules. Thus, vaccine delivery systems which can provide effective immunization after a single administration of the antigen delivery system have been sought. Many studies on vaccine delivery systems have been carried out with bacterial toxins, such as tetanus toxoid. See infra.

A protein incorporating implant can exhibit an initial burst of protein release, followed by a generally monophasic release thereafter. Unfortunately, due to the high concentration of protein within a controlled release matrix, the protein molecules can exhibit a tendency to aggregate and form denatured, immunogenic concentrations of protein.

Biodegradable microspheres implants for pulsatile release of a protein toxoid, such as a vaccine, are known. Thus, a solvent evaporation process has been used to make biodegradable, poly(lactic-co-glycolic acid) (PLGA) microspheres capable of providing either a continuous delivery of therapeutic proteins or a pulsatile delivery of protein vaccines with a triphasic release pattern. *Biotechnol Prog* 14(1):102–7:1998.

Additionally, biodegradable PLGA microspheres capable of pulsatile release of protein antigens, wherein the first pulse or pulse and the second pulse of antigen can be spaced by up to about six months apart are known. Hanes, J. et al., New Advances in Microsphere-Based Single-Dose Vaccines, Adv Drug Del Rev 28;97–119:1997.

Significantly, pulsed administration of a subunit vaccine (a recombinant glycoprotein) to HIV has been accomplished using poly(lactic-co-glycolic) acid (PLGA) microspheres. The immunizing pulses of protein vaccine can be timed to take place up to six month after implantation, such subsequent pulses of an antigen eliminating the need for repeated immunizations. *J Pharm Sci* 87(12):1489–95:1998.

Botulinum Toxin

The anaerobic, gram positive bacterium Clostridium botulinum produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can include nausea, difficulty walking and swallowing, and can progress to paralysis of respiratory muscles, cardiac failure and death.

Botulinum toxin type A is the most lethal natural biological agent known to man. About 50 picograms of a commercially available botulinum toxin type A (available from Allergan, Inc., Irvine, Calif. under the tradename BOTOX® (purified neurotoxin complex) in 100 unit vials) is a $LD_{50}$ in mice (i.e. 1 unit). Thus, one unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins,* pages 63–84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Neurotransmitters are packaged in synaptic vesicles within the cytoplasm of neurons and are then transported to the inner plasma membrane where the vesicles dock and fuse with the plasma membrane. Recent studies of nerve cells employing clostridial neurotoxins as probes of membrane fusion have revealed that fusion of synaptic vesicles with the cell membrane in nerve cells depends upon the presence of specific proteins that are associated with either the vesicle or the target membrane. These proteins have been termed SNAREs. A protein alternatively termed synaptobrevin or VAMP (vesicle-associated membrane protein) is a vesicle-associated SNARE (v-SNARE). There are at least two isoforms of synaptobrevin; these two isoforms are differentially expressed in the mammalian central nervous system, and are selectively associated with synaptic vesicles in neurons and secretory organelles in neuroendocrine cells. The target membrane-associated SNAREs (t-SNARES) include syntaxin and SNAP-25. Following docking, the VAMP protein forms a core complex with syntaxin and SNAP-25; the formation of the core complex appears to be an essential step to membrane fusion. See Neimann et al., *Trends in Cell Biol.* 4:179–185:1994.

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, and botulinum toxins B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype $C_1$ was originally thought to cleave syntaxin, but was found to cleave syntaxin and SNAP-25. Each toxin specifically cleaves a different bond (except tetanus and type B which cleave the same bond).

Botulinum toxins have been used in clinical settings for the treatment of neuromuscular disorders characterized by hyperactive skeletal muscles. Botulinum toxin type A was approved by the U.S. Food and Drug Administration in 1989 for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem, J 1;339 (pt 1):159–65:1999, and Mov Disord, 10(3): 376:1995 (pancreatic islet B cells contain at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., Tetanus Toxin and Botulinum A and C Neurotoxins Inhibit Noradrenaline Release From Cultured Mouse Brain, J Neurochem 51(2);522–527:1988) CGRP, substance P and glutamate (Sanchez-Prieto, J., et al., Botulinum Toxin A Blocks Glutamate Exocytosis From Guinea Pig Cerebral Cortical Synaptosomes, Eur J. Biochem 165;675–681:1987. Thus, when adequate concentrations are used, stimulus-evoked release of most neurotransmitters is blocked by botulinum toxin. See e.g. Pearce, L. B., Pharmacologic Characterization of Botulinum Toxin For Basic Science and Medicine, Toxicon 35(9);1373–1412 at 1393 (1997); Bigalke H., et al., Botulinum A Neurotoxin Inhibits Non-Cholinergic Synaptic Transmission in Mouse Spinal Cord Neurons in Culture, Brain Research 360;318–324:1985; Habermann E., Inhibition by Tetanus and Botulinum A Toxin of the Release of [$^3$H]Noradrenaline and [$^3$H]GABA From Rat Brain Homogenate, Experientia 44;224–226:1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244–251:1981, and; Jankovic J. et al., Therapy With Botulinum Toxin, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and Use of Botulinum Toxin and Other Microbial Neurotoxins in Medicine, Microbiol Rev.* 56;80–99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Botulinum toxins and/or botulinum toxin complexes can be obtained from various sources, including List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St. Louis, Mo.

Pure botulinum toxin is so labile that it is generally not used to prepare a pharmaceutical composition. Furthermore, the botulinum toxin complexes, such as the toxin type A complex are also extremely susceptible to denaturation due to surface denaturation, heat, and alkaline conditions. Inactivated toxin forms toxoid proteins which can be immunogenic. The resulting antibodies can render a patient refractory to toxin injection.

As with enzymes generally, the biological activities of the botulinum toxins (which are intracellular peptidases) are dependent, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Additionally, the toxin may be used months or years after the toxin containing pharmaceutical composition is formulated. Significantly, it is known that the toxin can be stabilized during the manufacture and compounding processes as well as during storage by use of a stabilizing agent such as albumin and gelatin.

The commercially available botulinum toxin sold under the trademark BOTOX® (available from Allergan, Inc., of Irvine, Calif.). BOTOX® consists of a freeze-dried, purified botulinum toxin type A complex, albumin and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® retains its potency for at least two weeks. *Neurology,* 48:249–53:1997.

It has been reported that botulinum toxin type A has been used in various clinical settings, including the following:
 (1) about 75–125 units of BOTOX® per intramuscular injection (multiple muscles) to treat cervical dystonia;
 (2) 5–10 units of BOTOX® per intramuscular injection to treat glabellar lines (brow furrows) (5 units injected intramuscularly into the procerus muscle and 10 units injected intramuscularly into each corrugator supercilii muscle);
 (3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111–S1150:1999), and in some circumstances for as long as 27 months, (*The Laryngoscope* 109: 1344–1346:1999). However, the usual duration of the paralytic effect of an intramuscular injection of Botox® is typically about 3 to 4 months.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. *Eur J Neurol* Nov. 6, 1999(Suppl 4):S3–S10.

In addition to having pharmacologic actions at a peripheral location, a botulinum toxin can also exhibit a denervation effect in the central nervous system. Wiegand et al, *Naunyn-Schmiedeberg's Arch. Pharmacol.* 1976; 292, 161–165, and Habermann, *Naunyn-Schmiedeberg's Arch. Pharmacol.* 1974; 281, 47–56 reported that botulinum toxin is able to ascend to the spinal area by retrograde transport. As such, a botulinum toxin injected at a peripheral location, for example intramuscularly, can potentially be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

At the present time, essentially all therapeutic use of a botulinum toxin is by subcutaneous or intramuscular injection of an aqueous solution of a botulinum toxin type A or B. Typically, a repeat injection must be administered every 2–4 months in order to maintain the therapeutic efficacy of the toxin (i.e. a reduction of muscle spasm at or in the vicinity of the injection site). Each administration of a dose of a botulinum toxin to a patient therefore requires the patient to present himself to his physician at regular intervals. Unfortunately, patients can forget or be unable to attend appointments and physician schedules can make regular, periodic care over a multiyear period difficult to consistently maintain. Additionally, the requirement for 3–6 toxin injections per year on an ongoing basis increases the risk of infection or of misdosing the patient.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Tetanus Toxoid Implants

The tetanus toxin bears many similarities to the botulinum toxins. Thus, both the tetanus toxin and the botulinum toxins are polypeptides made by closely related species of Clostridium (*Clostridium tetani* and *Clostridium botulinum,* respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., The Complete Sequence of Botulinum Neurotoxin Type A and Comparison with Other Clostridial Neurotoxins, J Biological Chemistry 265 (16);9153–9158:1990.

A toxoid is an antigen which can be used to raise antibodies to and thereby vaccinate against the toxin from which the toxoid is derived. Typically, the toxoid comprises the immunogenic fragment of the toxin (i.e. the carboxyl terminal of the heavy chain (designed as $H_C$) of the tetanus toxin or the botulinum toxins) or a toxin rendered biologically inactive, though still immunogenic, by thermal or chemical (i.e. formalin treatment) denaturation or alteration of the native toxin. Thus, unlike the natural toxin, the toxoid derived from the tetanus or botulinum toxin has been derived of its biological activity, that is its ability to act as an intracellular protease and inhibit neuronal exocytosis of acetylcholine.

Controlled release implants for the therapeutic administration of tetanus toxoid to achieve vaccination against tetanus toxin are known. Thus, the tetanus toxoid as a protein vaccine has been administered incorporated into injectable, biodegradable poly(lactide-co-glycolide) ("PLGA") microspheres. It has been determined that a water content of a lyophilized tetanus toxoid used to make a tetanus toxoid implant above about 10% can result in significant aggregation and inactivation of the tetanus toxoid. See e.g. pages 251–254 of Schwendeman S. P. et al., *Peptide, Protein, and Vaccine Delivery From Implantable Polymeric Systems,* chapter 12 (pages 229–267) of Park K., Controlled Drug Delivery Challenges and Strategies, American Chemical Society (1997).

Pulsatile tetanus toxoid implants which permit in vivo subcutaneous administration to mammals of four or five discrete doses (i.e. multiple pulses) of tetanus toxoid over a period in excess of 60 days are known. See e.g. Cardamone M., et al., In Vitro Testing of a Pulsatile Delivery System and its In Vivo Application for Immunization Against Tetanus Toxoid, J Controlled Release 47;205–219:1997.

To be fully immunized against tetanus it is believed to be essential for the patient to receive three consecutive doses of this antigen. Work has been carried out to develop a single dose (i.e. multi pulse) tetanus vaccine implant formulation. This has been achieved using PLA and PLGA microspheres which can release the vaccine in a controlled manner. Encapsulation of tetanus toxoid has been carried out using a water-in-oil-in-water solvent extraction and solvent evaporation techniques with a toxoid loading efficiency of greater than about 80%.

Albumin has been used to improve the stability of microsphere encapsulated protein. Thus, tetanus toxoid co-encapsulation with albumin has been shown to increase both the encapsulation efficiency into PLGA 50:50 (lactide:glycolide) microspheres and the immunogenicity of pulsatile release tetanus toxoid. Johansen P., et al., Improving Stability and Release Kinetics of Microencapsulated Tetanus Toxoid by Co-Encapsulation of Additives, Pharm Res 15(7);1103–1110:1998.

Attempts have been made to reduce encapsulated tetanus toxoid inactivation by polymer degradation products by making PLGA and poloxamer 188 (a non-ionic surfactant) blend microspheres through an oil-in-oil extraction process, the poloxamer 188 reportedly acting to prevent interaction between antigen and polymer. Tobio M., et al., A Novel System Based on a Poloxamer/PLGA Blend as a Tetanus Toxoid Delivery Vehicle, Pharm Res 16(5);682–688:1999.

It is known to combine a plurality of discrete sets of tetanus toxoid incorporating microspheres into a single implant, wherein each set of microspheres has a different polymeric composition and hence a different rate of biodegradation, to thereby provide a pulsatile (multiple pulse) release tetanus toxoid implant. Thus, mice have been injected with a 5% lecithin solution (total volume 100 μl/injection) comprising three discrete set of tetanus toxin incorporating biodegradable, polymeric microspheres. The microspheres used were: (1) poly(D,L-lactide-co-glycolide) (PLGA) where the lactide and glycolide copolymers were present in a 50:50 ratio; (2) PLGA 75:25 microspheres, and; (3) poly(D,L-lactide) (PLA) 100:0 microspheres. Lecithin was used to disperse the microspheres. The PLGA 50:50 and the PLGA 75:25 microspheres both showed an initial burst release (over one day) of between 30–40% of the total dose of tetanus toxoid. The remaining tetanus toxoid was delivered between 3–5 weeks after injection from the PLGA 50:50 microspheres and between 8–12 weeks for the PLGA 75:25 microspheres. The PLA 100:0 microspheres did not give an initial burst release, but rather a release of the tetanus toxoid antigen over 4–6 months. Thus, use of a single injection of a mixture of three different tetanus toxoid incorporating microspheres provided four pulses of the tetanus toxoid over a six month period: a first pulse due to the day one burst, a second pulse during weeks 3–5, a third pulse during weeks 8–12 and a fourth pulse during months 4–6. Men Y., et al., G., A Single Administration of Tetanus Toxoid in Biodegradable Microspheres Elicits T Cell and Antibody Responses Similar or Superior to Those Obtained with Aluminum Hydroxide, Vaccine 13, 683–689:1995.

Tetanus and botulinum toxoid vaccines have been made by treating the native toxin with formalin. The U.S. Center for Disease Control can supply a pentavalent, formalin-inactivated toxoid of botulinum toxin types A, B, C, D and E. The pre-exposure immunization schedule calls for subcutaneous administration of the botulinum toxoid vaccine in three dosings at 0, 2 and 12 weeks with a booster at plus 12 months and yearly boasters at yearly intervals thereafter if antibody levels fall.

U.S. Pat. No. 5,980,948 discusses use of polyetherester copolymer microspheres for encapsulation and controlled delivery of a variety of protein drugs, including tetanus and botulinum antitoxins.

U.S. Pat. No. 5,902,565 discusses A controlled or delayed-release preparation comprising microspherical particles comprising a continuous matrix of biodegradable polymer containing discrete, immunogen-containing regions, where the immunogens can be botulinum toxin type C and D toxoids.

What is needed therefore is a biocompatible, pulsatile release, botulinum toxin delivery system by which therapeutic amounts of the botulinum toxin can be locally administered in vivo to a human patient over a prolonged period of time.

SUMMARY

The present invention meets this need and provides a biocompatible, pulsatile release, botulinum toxin delivery system by which therapeutic amounts of the botulinum toxin can be locally administered in vivo to a human patient over a prolonged period of time.

The present invention provides a botulinum toxin implant which overcomes the known problems, difficulties and deficiencies associated with repetitive bolus or subcutaneous injection of a botulinum toxin, to treat an affliction such as a movement disorder, including a muscle spasm.

A pulsatile release botulinum toxin delivery system within the scope of the present invention can comprise a carrier material and a botulinum toxin associated with the carrier. The toxin can be associated with the carrier by being mixed with and encapsulated by the carrier to thereby form a pulsatile release botulinum toxin delivery system, that is a botulinum toxin implant. The implant can release therapeutic amounts of the botulinum toxin from the carrier in a plurality of pulses in vivo upon subdermal implantation of the implant system into a human patient. "Subdermal" implantation includes subcutaneous, intramuscular, intraglandular and intracranial sites of implantation.

Preferably, the carrier comprises a plurality of polymeric microspheres (i.e. a polymeric matrix) and substantial amounts of the botulinum toxin has not be transformed into a botulinum toxoid prior to association of the botulinum toxin with the carrier. That is, significant amounts of the botulinum toxin associated with the carrier have a toxicity which is substantially unchanged relative to the toxicity of the botulinum toxin prior to association of the botulinum toxin with the carrier.

According to the present invention, the botulinum toxin can be released from the carrier over of a period of time of from about 10 days to about 6 years and the carrier is comprised of a substance which is substantially biodegradable.

The botulinum toxin is one of the botulinum toxin types A, B, $C_1$, D, E, F and G and is preferably botulinum toxin type A. The botulinum toxin can be associated with the carrier in an amount of between about 1 unit and about 50,000 units of the botulinum toxin. Preferably, the quantity of the botulinum toxin associated with the carrier is between about 10 units and about 2,000 units of a botulinum toxin type A. Where the botulinum toxin is botulinum toxin type B, preferably, the quantity of the botulinum toxin associated with the carrier is between about 100 units and about 30,000 units of a botulinum toxin type B.

A detailed embodiment of the present invention can comprise a controlled release system, comprising a biodegradable polymer and between about 10 units and about 100,000 units of a botulinum toxin encapsulated by the polymer carrier, thereby forming a controlled release system, wherein therapeutic amounts of the botulinum toxin can be released from the carrier in a pulsatile manner in vivo upon subdermal implantation of the controlled release system in a human patient over a prolonged period of time extending from about 2 months to about 5 years.

A method for making an implant within the scope of the present invention can have the steps of: dissolving a polymer in a solvent to form a polymer solution; mixing or dispersing a botulinum toxin in the polymer solution to form a polymer-botulinum toxin mixture, and; allowing the polymer-botulinum toxin mixture to set or cure, thereby making an implant for pulsatile release of the botulinum toxin. This method can have the further step after the mixing step of evaporating solvent.

A method for using a pulsatile implant within the scope of the present invention can be by injecting or implanting a polymeric implant which includes a botulinum toxin, thereby treating a movement disorder or a disorder influenced by cholinergic innervation by local administration of a botulinum toxin.

An alternate embodiment of the present invention can be a carrier comprising a polymer selected from the group of polymers consisting of polylactides and polyglycolides and a stabilized botulinum toxin associated with the carrier, thereby forming a pulsatile release botulinum toxin delivery system, wherein therapeutic amounts of the botulinum toxin can be released from the carrier in a plurality of pulses in vivo upon subdermal implantation of the delivery system in a human patient. The carrier can comprise a plurality of discrete sets of polymeric, botulinum toxin incorporating microspheres, wherein each set of polymers has a different polymeric composition.

The botulinum toxin used in an implant according to the present invention can comprise: a first element comprising a binding element able to specifically bind to a neuronal cell surface receptor under physiological conditions, a second element comprising a translocation element able to facilitate the transfer of a polypeptide across a neuronal cell membrane, and a third element comprising a therapeutic element able, when present in the cytoplasm of a neuron, to inhibit exocytosis of acetylcholine from the neuron. The therapeutic element can cleave a SNARE protein, thereby inhibiting the exocytosis of acetylcholine from the neuron and the SNARE protein is can be selected from the group consisting of syntaxin, SNAP-25 and VAMP. Generally, the neuron affected by the botulinum toxin is a presynaptic, cholinergic, peripheral motor neuron.

The amount of a botulinum toxin administered by a continuous release system within the scope of the present invention during a given period can be between about $10^{-3}$ U/kg and about 35 U/kg for a botulinum toxin type A and up to about 2000 U/kg for other botulinum toxins, such as a botulinum toxin type B. 35 U/kg or 2000 U/kg is an upper limit because it approaches a lethal dose of certain neurotoxins, such as botulinum toxin type A or botulinum toxin type B, respectively. Thus, it has been reported that about 2000 units/kg of a commercially available botulinum toxin type B preparation approaches a primate lethal dose of type B botulinum toxin. Meyer K. E. et al, A Comparative Systemic Toxicity Study of Neurobloc in Adult Juvenile Cynomolgus Monkeys, Mov. Disord 15(Suppl 2);54;2000.

Preferably, the amount of a type A botulinum toxin administered by a continuous release system during a given period is between about $10^{-2}$ U/kg and about 25 U/kg. Preferably, the amount of a type B botulinum toxin administered by a continuous release system during a given period is between about $10^{-2}$ U/kg and about 1000 U/kg, since it has been reported that less than about 1000 U/kg of type B botulinum toxin can be intramuscularly administered to a primate without systemic effect. Ibid. More preferably, the type A botulinum toxin is administered in an amount of between about $10^{-1}$ U/kg and about 15 U/kg. Most preferably, the type A botulinum toxin is administered in an amount of between about 1 U/kg and about 10 U/kg. In many instances, an administration of from about 1 units to about 500 units of a botulinum toxin type A, provides effective and long lasting therapeutic relief. More preferably, from about 5 units to about 300 units of a botulinum toxin, such as a botulinum toxin type A, can be used and most preferably, from about 10 units to about 200 units of a neurotoxin, such as a botulinum toxin type A, can be locally administered into a target tissue with efficacious results. In a particularly preferred embodiment of the present invention from about 1 units to about 100 units of a botulinum toxin, such as botulinum toxin type A, can be locally administered into a target tissue with therapeutically effective results.

The botulinum toxin can be made by *Clostridium botulinum*. Additionally, the botulinum toxin can be a modified botulinum toxin, that is a botulinum toxin that has at least one of its amino acids deleted, modified or replaced, as compared to the native or wild type botulinum toxin. Furthermore, the botulinum toxin can be a recombinant produced botulinum toxin or a derivative or fragment thereof.

Significantly, the botulinum toxin can be is administered to by subdermal implantation to the patient by placement of a botulinum toxin implant. The botulinum toxin can administered to a muscle of a patient in an amount of between about 1 unit and about 10,000 units. When the botulinum toxin is botulinum toxin type A and the botulinum toxin can be administered to a muscle of the patient in an amount of between about 1 unit and about 100 units.

Notably, it has been reported that glandular tissue treated by a botulinum toxin can show a reduced secretory activity for as long as 27 months post injection of the toxin. *Laryngoscope* 1999; 109:1344–1346, *Laryngoscope* 1998;108:381–384.

The present invention relates to an implant for the controlled release of a neurotoxin and to methods for making and using such implants. The implant can comprise a polymer matrix containing a botulinum toxin. The implant is designed to administer effective levels of neurotoxin over a prolonged period of time when administered, for example, intramuscularly, epidurally or subcutaneously for the treatment of various diseases conditions.

This invention further relates to a composition, and methods of making and using the composition, for the controlled of biologically active, stabilized neurotoxin. The controlled release composition of this invention can comprise a polymeric matrix of a biocompatible polymer and biologically active, stabilized neurotoxin dispersed within the biocompatible polymer.

Definitions

The following definitions apply herein.

"About" means plus or minus ten percent of the value so qualified.

"Biocompatible" means that there is an insignificant inflammatory response at the site of implantation from use of the implant.

"Biologically active compound" means a compound which can effect a beneficial change in the subject to which it is administered. For example, "biologically active compounds" include neurotoxins.

"Effective amount" as applied to the biologically active compound means that amount of the compound which is generally sufficient to effect a desired change in the subject. For example, where the desired effect is a flaccid muscle paralysis, an effective amount of the compound is that amount which causes at least a substantial paralysis of the desired muscles without causing a substantial paralysis of adjacent muscle of which paralysis is not desired, and without resulting in a significant systemic toxicity reaction.

"Effective amount" as applied to a non-active ingredient constituent of an implant (such as a polymer used for forming a matrix or a coating composition) refers to that amount of the non-active ingredient constituent which is sufficient to positively influence the release of a biologically active agent at a desired rate for a desired period of time. For example, where the desired effect is muscle paralysis by using a single implant, the "effective amount" is the amount that can facilitate extending the release over a period of between about 60 days and 6 years. This "effective amount" can be determined based on the teaching in this specification and the general knowledge in the art.

"Effective amount" as applied to the amount of surface area of an implant is that amount of implant surface area which is sufficient to effect a flux of biologically active compound so as to achieve a desired effect, such as a muscle paralysis. The area necessary may be determined and adjusted directly by measuring the release obtained for the particular active compound. The surface area of the implant or of a coating of an implant is that amount of membrane necessary to completely encapsulate the biologically active compound. The surface area depends on the geometry of the implant. Preferably, the surface area is minimized where possible, to reduce the size of the implant.

"Implant" means a controlled release (i.e. pulsatile) drug delivery system. The implant is comprised of a biocompatible polymer or ceramic material which contains or which can act as a carrier for a molecule with a biological activity. The implant can be, injected, inserted or implanted into a human body.

"Local administration" means direct administration of a biologically active compound, such as a therapeutic drug to a tissue by a non-systemic route. Local administration therefore includes, subcutaneous, intramuscular, intraspinal (i.e. intrathecal and epidural), intracranial, and intraglandular administration. Local administration excludes a systemic route of administration such as oral or intravenous administration.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

A method for making an implant within the scope of the present invention for controlled release of a neurotoxin, can include dissolving a biocompatible polymer in a polymer solvent to form a polymer solution, dispersing particles of biologically active, stabilized neurotoxin in the polymer solution, and then solidifying the polymer to form a polymeric matrix containing a dispersion of the neurotoxin particles.

A method of using an implant within the scope of the present invention forming for controlled release of a neurotoxin can comprise providing a therapeutically effective level of biologically active, neurotoxin in a patient for a prolonged period of time by implanting in the patient the implant.

Description

The present invention is based upon the discovery of a pulsatile release implant comprising a biocompatible, biodegradable polymer capable of exhibiting in vivo multiphasic release of therapeutic amounts of a botulinum toxin over a prolonged period of tome.

A botulinum toxin delivery system within the scope of the present invention is capable of pulsatile (i.e. multiphasic) release of therapeutic amounts of a botulinum toxin. By pulsatile release it is meant that during a period of time, which can extend from about 1 hour to about 4 weeks, a quantity of therapeutically effective (i.e. biologically active) botulinum toxin is released from a carrier material in vivo at the site of implantation. The pulse of released botulinum toxin can comprise (for a botulinum toxin type A) as little as about 1 unit (i.e. to treat blepharospasm) to as much as 200 units (i.e. to treat of a large spasmodic muscle, such as the biceps). The quantity of botulinum toxin required for therapeutic efficacy can be varied according to the known clinical potency of the different botulinum toxin serotypes. For example, several orders of magnitude more units of a botulinum toxin type B are typically required to achieve a physiological effect comparable to that achieved from use of a botulinum toxin type A. Prior to and following each pulse there is a period of reduced or substantially no botulinum toxin release from the implant.

The botulinum toxin released in therapeutically effective amounts by a controlled release delivery system within the scope of the present invention is preferably, substantially biologically active botulinum toxin. In other words, the botulinum toxin released from the disclosed delivery system is capable of binding with high affinity to a cholinergic neuron, being translocated, at least in part, across the neuronal membrane, and through its activity in the cytosol of the neuron of inhibiting exocytosis of acetylcholine from the neuron. The present invention excludes from its scope use deliberate use of a botulinum toxoid as an antigen in order to confer immunity to the botulinum toxin through development of antibodies (immune response) due to the immunogenicity of the toxoid. The purpose of the present invention is to permit a controlled release of minute amounts of a botulinum toxin from a delivery system so as to inhibit exocytosis in vivo and thereby achieve a desired therapeutic effect, such as reduction of muscle spasm or muscle tone, preventing a muscle from contracting or to reduce an excessive secretion (i.e. a sweat secretion) from a cholinergically influenced secretory cell or gland.

Pulsatile release of a botulinum toxin from an implant can be accomplished by preparing a plurality of implants with differing carrier material compositions. For example, holding other factors, such as polymer molecular weight, constant an implant can be made up of a several sets of botulinum toxin encapsulated microspheres, each set of microspheres having a different polymer composition such that the polymers of each set of microspheres degrade, and release toxin, at differing rates. Conveniently, the plurality of sets of differing polymer composition microspheres can be pressed into the form of a disc, and implanted as a pellet. The pulsatile release implant can be implanted subcutaneously, intramuscularly, intracranially, intraglandular, etc, at a site so that systemic entry of the toxin is not encouraged.

A first pulse of a botulinum toxin can be locally administered due to the presence of a botulinum toxin (i.e. free or non-implant incorporated botulinum toxin) administered in conjunction with and at the same time as insertion of the implant and/or due to a burst effect of botulinum toxin release from the implanted microspheres. A second pulse of a botulinum toxin can be administered by the implant at about three months post implantation upon biodegradation of a first set of microspheres. A third pulse of a botulinum toxin can be delivered by the system at about six months post implantation upon dissolution of a second set of bioerodible microspheres, and so on. Thus, a botulinum toxin delivery system within the scope of the present invention which comprises three differing sets of appropriate microsphere polymer compositions, permits a patient to be reimplant or reinvested with a botulinum toxin only once every 12 months.

For example, it is known that biodegradable PLA:PGA microspheres can be made with varying copolymer content such that proportionally different polymer degradation time windows result. Thus, a 75:25 lactide:glycolide polymer can degrade at about ninety days post implantation. Additionally, a 100:0 lactide:glycolide polymer can degrade at about one hundred and eighty days post implantation. Furthermore, a 95:5 poly(DL-lactide):glycolide polymer can degrade at about two hindered and seventy days post implantation. Finally, a 100:0 poly(DL-lactide):glycolide polymer can degrade at about twelve months post implantation. See e.g. Kissel et al, Microencapsulation of Antigens Using Biodegradable Polymers: Facts and Fantasies, Behring Inst. Mitt., 98;172–183:1997; Cleland J. L., et al, Development of a Single-Shot Subunit Vaccine for HOV-1: Part 4. Optimizing Microencapsulation and Pulsatile Release of MN rpg120 from Biodegradable Microspheres, J Cont Rel 47;135–150:1997, and; Lewis D. H., *Controlled Release of Bioactive Agents from Lactide/Glycolide Polymers*, pages 1–41 of Chasin M., et al, "Biodegradable Polymers as Drug-Delivery Systems", Marcel Dekker, New York (1990). The above-specified four discrete sets of polymeric microspheres can be prepared as botulinum toxin incorporating microspheres, and combined into a single implant capable of pulsatile release of the botulinum toxin over a one year period, thereby providing a patient treatment period per implant of about 15–16 months.

The delivery system is prepared so that the botulinum toxin is substantially uniformly dispersed in a biodegradable carrier. An alternate pulsatile delivery system within the scope of the present invention can comprise a carrier coated by a biodegradable coating, either the thickness of the coating or the coating material being varied, such that in the different sets of microspheres, the respective coating take from 3, 6, 9, etc months to be dissolved, thereby providing the desired toxin pulses. The microspheres are inert and are of such a size or due to being pressed into a disc, that they do no diffuse significantly beyond the site of injection. Hence, multiple implantations, as by needle injection, can be carried out at the same time.

A third embodiment within the scope of the present invention of a pulsatile, implant can comprise a non-porous, non-biodegradable, biocompatible tube which is closed at one end. Carrier associated neurotoxin is interspaced discrete locations within the bore of the tube. Thus, toxin at an open or porous, or erodible plug sealed pug the end of the tube rapidly diffuses out, causing the first local administration. Toxin further from the end of the tube takes longer to diffuse out and results in the second local.

The thickness of the implant can be used to control the absorption of water by, and thus the rate of release of a neurotoxin from, a composition of the invention, thicker implants releasing the polypeptide more slowly than thinner ones.

The neurotoxin in a neurotoxin controlled release composition can also be mixed with other excipients, such as bulking agents or additional stabilizing agents, such as buffers to stabilize the neurotoxin during lyophilization.

The carrier is preferably comprised of a non-toxic, non-immunological, biocompatible material. Suitable the implant materials can include polymers of poly(2-hydroxy ethyl methacrylate) (p-HEMA), poly(N-vinyl pyrrolidone) (p-NVP)+, poly(vinyl alcohol) (PVA), poly(acrylic acid) (PAA), polydimethyl siloxanes (PDMS), ethylene-vinyl acetate copolymers (EVAc), a polymethylmethacrylate (PMMA), polyvinylpyrrolidone/methylacrylate copolymers, poly(lactic acid) (PLA), poly(glycolic acid) (PGA), polyanhydrides, poly(ortho esters), collagen and cellulosic derivatives and bioceramics, such as hydroxyapatite (HPA), tricalcium phosphate (TCP), and aliminocalcium phosphate (ALCAP).

Biodegradable carriers can be made from polymers of poly(lactides), poly(glycolides), collagens, poly(lactide-co-glycolides), poly(lactic acid)s, poly(glycolic acid)s, poly (lactic acid-co-glycolic acid)s, polycaprolactone, polycarbonates, polyesteramides, polyanhydrides, poly (amino acids), polyorthoesters, polycyanoacrylates, poly(p-dioxanone), poly(alkylene oxalates), biodegradable polyurethanes, blends and copolymers thereof. Particularly preferred carriers are formed as polymers or copolymers of poly(lactic-co-glycolic acid) ("PLGA"), where the lactide-:glycolide ratio can be varied depending on the desired carrier degradation rate.

Biodegradable PLGA polymers have been used to form resorbable sutures and bone plates and in several commercial microparticle formulations. PLGA degrades through bulk erosion to produce lactic and glycolic acid and is commercially available in a variety of molecular weight and polymer end groups (e.g. lauryl alcohol or free acid). Polyanhydrides are another group of polymers that have been approved for use I humans, and have been used to deliver proteins and antigens. Unlike PLGA, polyanhydrides degrade by surface erosion, releasing neurotoxin entrapped at the carrier surface.

To prepare a suitable implant, the carrier polymer is dissolved in an organic solvent such as methylene chloride or ethyl acetate and the botulinum toxin is then mixed into the polymer solution. The conventional processes for microsphere formation are solvent evaporation and solvent (coacervation) methods. The water-in-oil-in-water (W/O/W)

double emulsion method is a widely used method of protein antigen encapsulation into PLGA microspheres.

An aqueous solution of a botulinum toxin can be used to make a pulsatile implant. An aqueous solution of the neurotoxin is added to the polymer solution (polymer previously dissolved in a suitable organic solvent). The volume of the aqueous (neurotoxin) solution relative to the volume of organic (polymer) solvent is an important parameter in the determination of both the release characteristics of the microspheres and with regard to the encapsulation efficiency (ratio of theoretical to experimental protein loading) of the neurotoxin.

The encapsulation efficiency can also be increased by increasing the kinematic viscosity of the polymer solution. The kinematic viscosity of the polymer solution can be increased by decreasing the operating temperature and/or by increasing the polymer concentration in the organic solvent.

Thus, with a low aqueous phase (neurotoxin) to organic phase (polymer) volume ratio (i.e. aqueous volume:organic volume is $\leq 0.1$ ml/ml) essentially 100% of the neurotoxin can be encapsulated by the microspheres and the microspheres can show a triphasic release: an initial burst (first pulse), a lag phase with little or no neurotoxin being released and a second release phase (second pulse).

The length of the lag phase is dependent upon the polymer degradation rate which is in turn dependant upon polymer composition and molecular weight. Thus, the lag phase between the first (burst) pulse and the second pulse increases as the lactide content is increased, or as the polymer molecular weight is increased with the lactide:glycolide ratio being held constant. In addition to a low aqueous phase (neurotoxin) volume, operation at low temperature (2–8 degrees C.), as set forth above, increases the encapsulation efficiency, as well as reducing the initial burst and promoting increased neurotoxin stability against thermal inactivation.

Suitable implants within the scope of the present invention for the controlled in vivo release of a neurotoxin, such as a botulinum toxin, can be prepared so that the implant releases the neurotoxin in a pulsatile manner. A pulsatile release implant can release a neurotoxin is a biphasic or multiphase manner. Thus, a pulsatile release implant can have a relatively short initial induction (burst) period, followed by periods during which reduced, little or no neurotoxin is released.

A controlled release of biologically active neurotoxin is a release which results in therapeutically effective, with negligible serum levels, of biologically active, neurotoxin over a period longer than that obtained following direct administration of aqueous neurotoxin. It is preferred that a controlled release be a release of neurotoxin for a period of about six months or more, and more preferably for a period of about one year or more.

An implant within the scope of the present invention can also be formulated as a suspension for injection. Such suspensions may be manufactured by general techniques well known in the pharmaceutical art, for example by milling the polylactide/polypeptide mixture in an ultracentrifuge mill fitted with a suitable mesh screen, for example a 120 mesh, and suspending the milled, screened particles in a solvent for injection, for example propylene glycol, water optionally with a conventional viscosity increasing or suspending agent, oils or other known, suitable liquid vehicles for injection.

Denaturation of the encapsulated neurotoxin in the body at 37 degrees C. for a prolonged period of time can be reduced by stabilizing the neurotoxin by lyophilizing it with albumin, lyophilizing from an acidic solution, lyophilizing from a low moisture content solution (these three criteria can be met with regard to a botulinum toxin type A by use of non-reconstituted Botox®) and using a specific polymer matrix composition.

Preferably, the release of biologically active neurotoxin in vivo does not result in a significant immune system response during the release period of the neurotoxin.

A pulsatile botulinum toxin delivery system preferably permits botulinum release from biodegradable polymer microspheres in a biologically active form, that is with a substantially native toxin conformation. To stabilize a neurotoxin, both in a format which renders the neurotoxin useful for mixing with a suitable polymer which can form the implant matrix (i.e. a powdered neurotoxin which has been freeze dried or lyophilized) as well as while the neurotoxin is present or incorporated into the matrix of the selected polymer, various pharmaceutical excipients can be used. Suitable excipients can include starch, cellulose, talc, glucose, lactose, sucrose, gelatin, malt, rice, flour, chalk, silica gel, magnesium stearate, sodium stearate, glycerol monostearate, sodium chloride, albumin and dried skim milk. The neurotoxin in a neurotoxin controlled release composition can be mixed with excipients, bulking agents and stabilizing agents, and buffers to stabilize the neurotoxin during lyophilization or freeze drying.

It has been discovered that a stabilized neurotoxin can comprise biologically active, non-aggregated neurotoxin complexed with at least one type of multivalent metal cation which has a valiancy of +2 or more.

Suitable multivalent metal cations include metal cations contained in biocompatible metal cation components. A metal cation component is biocompatible if the cation component is non-toxic to the recipient, in the quantities used, and also presents no significant deleterious or untoward effects on the recipient's body, such as an immunological reaction at the injection site.

Preferably, the molar ratio of metal cation component to neurotoxin, for the metal cation stabilizing the neurotoxin, is between about 4:1 to about 100:1 and more typically about 4:1 to about 10:1.

A preferred metal cation used to stabilize a botulinum toxin is $Zn^{++}$ because the botulinum toxin are known to be zinc endopeptidases. Divalent zinc cations are preferred because botulinum toxin is known to be a divalent zinc endopeptidase. In a more preferred embodiment, the molar ratio of metal cation component, containing $Zn^{++}$ cations, to neurotoxin is about 6:1.

The suitability of a metal cation for stabilizing neurotoxin can be determined by one of ordinary skill in the art by performing a variety of stability indicating techniques such as polyacrylamide gel electrophoresis, isoelectric focusing, reverse phase chromatography, HPLC and potency tests on neurotoxin lyophilized particles containing metal cations to determine the potency of the neurotoxin after lyophilization and for the duration of release from microparticles. In stabilized neurotoxin, the tendency of neurotoxin to aggregate within a microparticle during hydration in vivo and/or to lose biological activity or potency due to hydration or due to the process of forming a controlled release composition, or due to the chemical characteristics of a controlled release composition, is reduced by complexing at least one type of metal cation with neurotoxin prior to contacting the neurotoxin with a polymer solution.

By the present invention, stabilized neurotoxin is stabilized against significant aggregation in vivo over the controlled release period. Significant aggregation is defined as an amount of aggregation resulting in aggregation of about 15% or more of the polymer encapsulated or polymer matrix incorporated neurotoxin. Preferably, aggregation is maintained below about 5% of the neurotoxin. More preferably, aggregation is maintained below about 2% of the neurotoxin present in the polymer.

In another embodiment, a neurotoxin controlled release composition also contains a second metal cation component, which is not contained in the stabilized neurotoxin particles, and which is dispersed within the polymer. The second metal cation component preferably contains the same species of metal cation, as is contained in the stabilized neurotoxin. Alternately, the second metal cation component can contain one or more different species of metal cation.

The second metal cation component acts to modulate the release of the neurotoxin from the polymeric matrix of the controlled release composition, such as by acting as a reservoir of metal cations to further lengthen the period of time over which the neurotoxin is stabilized by a metal cation to enhance the stability of neurotoxin in the composition.

A metal cation component used in modulating release typically contains at least one type of multivalent metal cation. Examples of second metal cation components suitable to modulate neurotoxin release, include, or contain, for instance, $Mg(OH)_2$, $MgCO_3$ (such as $4MgCO_3Mg(OH)_2 5H_2O$), $ZnCO_3$(such as $3Zn(OH)_2 2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3 (C_6H_5O_7)_2$. A suitable ratio of second metal cation component-to-polymer is between about 1:99 to about 1:2 by weight. The optimum ratio depends upon the polymer and the second metal cation component utilized.

The neurotoxin controlled release composition of this invention can be formed into many shapes such as a film, a pellet, a cylinder, a disc or a microsphere. A microsphere, as defined herein, comprises a polymeric component having a diameter of less than about one millimeter and having stabilized neurotoxin dispersed therein. A microsphere can have a spherical, non-spherical or irregular shape. It is preferred that a microsphere be spherical in shape. Typically, the microsphere will be of a size suitable for injection. A preferred size range for microspheres is from about 1 to about 180 microns in diameter.

In the method of this invention for forming a composition for the controlled release of biologically active, non-aggregated neurotoxin, a suitable amount of particles of biologically active, stabilized neurotoxin are dispersed in a polymer solution.

A suitable polymer solvent, as defined herein, is solvent in which the polymer is soluble but in which the stabilized neurotoxin is are substantially insoluble and non-reactive. Examples of suitable polymer solvents include polar organic liquids, such as methylene chloride, chloroform, ethyl acetate and acetone.

To prepare biologically active, stabilized neurotoxin, neurotoxin is mixed in a suitable aqueous solvent with at least one suitable metal cation component under pH conditions suitable for forming a complex of metal cation and neurotoxin. Typically, the complexed neurotoxin will be in the form of a cloudy precipitate, which is suspended in the solvent. However, the complexed neurotoxin can also be in solution. In an even more preferred embodiment, neurotoxin is complexed with $Zn^{++}$.

Suitable pH conditions to form a complex of neurotoxin typically include pH values between about 5.0 and about 6.9. Suitable pH conditions are typically achieved through use of an aqueous buffer, such as sodium bicarbonate, as the solvent.

Suitable solvents are those in which the neurotoxin and the metal cation component are each at least slightly soluble, such as in an aqueous sodium bicarbonate buffer. For aqueous solvents, it is preferred that water used be either deionized water or water-for-injection (WFI).

The neurotoxin can be in a solid or a dissolved state, prior to being contacted with the metal cation component. Additionally, the metal cation component can be in a solid or a dissolved state, prior to being contacted with the neurotoxin. In a preferred embodiment, a buffered aqueous solution of neurotoxin is mixed with an aqueous solution of the metal cation component.

Typically, the complexed neurotoxin will be in the form of a cloudy precipitate, which is suspended in the solvent. However, the complexed neurotoxin can also be in solution. In a preferred embodiment, the neurotoxin is complexed with $Zn^{++}$.

The $Zn^{++}$ complexed neurotoxin can then be dried, such as by lyophilization, to form particulates of stabilized neurotoxin. The $Zn^{++}$ complexed neurotoxin, which is suspended or in solution, can be bulk lyophilized or can be divided into smaller volumes which are then lyophilized. In a preferred embodiment, the $Zn^{++}$ complexed neurotoxin suspension is micronized, such as by use of an ultrasonic nozzle, and then lyophilized to form stabilized neurotoxin particles. Acceptable means to lyophilize the $Zn^{++}$ complexed neurotoxin mixture include those known in the art.

In another embodiment, a second metal cation component, which is not contained in the stabilized neurotoxin particles, is also dispersed within the polymer solution.

It is understood that a second metal cation component and stabilized neurotoxin can be dispersed into a polymer solution sequentially, in reverse order, intermittently, separately or through concurrent additions. Alternately, a polymer, a second metal cation component and stabilized neurotoxin and can be mixed into a polymer solvent sequentially, in reverse order, intermittently, separately or through concurrent additions. In this method, the polymer solvent is then solidified to form a polymeric matrix containing a dispersion of stabilized neurotoxins.

A suitable method for forming an neurotoxin controlled release composition from a polymer solution is the solvent evaporation method is described in U.S. Pat. Nos. 3,737,337; 3,523,906; 3,691,090, and; 4,389,330. Solvent evaporation can be used as a method to form neurotoxin controlled release microparticles.

In the solvent evaporation method, a polymer solution containing a stabilized neurotoxin particle dispersion, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of stabilized neurotoxin particles contained therein.

A preferred method for forming neurotoxin controlled release microspheres from a polymer solution is described in U.S. Pat. No. 5,019,400. This method of microsphere formation, as compared to other methods, such as phase separation, additionally reduces the amount of neurotoxin required to produce a controlled release composition with a specific neurotoxin content.

In this method, the polymer solution, containing the stabilized neurotoxin dispersion, is processed to create droplets, wherein at least a significant portion of the droplets contain polymer solution and the stabilized neurotoxin. These droplets are then frozen by means suitable to form microspheres. Examples of means for processing the polymer solution dispersion to form droplets include directing the dispersion through an ultrasonic nozzle, pressure nozzle, Rayleigh jet, or by other known means for creating droplets from a solution.

The solvent in the frozen microdroplets is extracted as a solid and/or liquid into the non-solvent to form stabilized neurotoxin containing microspheres. Mixing ethanol with other non-solvents, such as hexane or pentane, can increase the rate of solvent extraction, above that achieved by ethanol alone, from certain polymers, such as poly(lactide-co-glycolide) polymers.

Yet another method of forming a neurotoxin implant, from a polymer solution, includes film casting, such as in a mold, to form a film or a shape. For instance, after putting the polymer solution containing a dispersion of stabilized neurotoxin into a mold, the polymer solvent is then removed by means known in the art, or the temperature of the polymer solution is reduced, until a film or shape, with a consistent dry weight, is obtained.

In the case of a biodegradable polymer implant, release of neurotoxin due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of a biodegradable polymer, the contributions of diffusion and/or polymer degradation to neurotoxin release can be controlled. For example, increasing the glycolide content of a poly(lactide-co-glycolide) polymer and decreasing the molecular weight of the polymer can enhance the hydrolysis of the polymer and thus, provides an increased neurotoxin release from polymer erosion. In addition, the rate of polymer hydrolysis is increased in non-neutral pH's. Therefore, an acidic or a basic excipient can be added to the polymer solution, used to form the microsphere, to alter the polymer erosion rate.

An implant within the scope of the present invention can be administered to a human, or other animal, by any non-systemic means of administration, such as by implantation (e.g. subcutaneously, intramuscularly, intracranially, intravaginally and intradermally), to provide the desired dosage of neurotoxin based on the known parameters for treatment with neurotoxin of various medical conditions, as previously set forth.

The specific dosage by implant appropriate for administration is readily determined by one of ordinary skill in the art according to the factor discussed above. The dosage can also depend upon the size of the tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 units per kilogram to about 35 units per kg of patient weight of a botulinum toxin, such as botulinum toxin type A, can be released by the present implant per unit time period (i.e. over a period of or once every 2–4 months) to effectively accomplish a desired muscle paralysis. Less than about 0.01 U/kg of a botulinum toxin does not have a significant therapeutic effect upon a muscle, while more than about 35 U/kg of a botulinum toxin approaches a toxic dose of a neurotoxin, such as a botulinum toxin type A. Careful preparation and placement of the implant prevents significant amounts of a botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the tissue to be treated and the administration route chosen. Botulinum toxin type A is a preferred botulinum toxin serotype for use in the methods of the present invention.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when used to treat a movement disorder or an affliction influenced by cholinergic innervation. For example, neurotoxins made by any of the species of the toxin producing Clostridium bacteria, such as *Clostridium botulinum, Clostridium butyricum,* and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide effective relief for from 1 month to about 5 or 6 years.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on a cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

The present invention also includes within its scope the use of an implanted controlled release neurotoxin complex so as to provide therapeutic relief from a chronic disorder such as movement disorder. Thus, the neurotoxin can be imbedded within, absorbed, or carried by a suitable polymer matrix which can be implanted or embedded subdermally so as to provide a year or more of delayed and controlled release of the neurotoxin to the desired target tissue. Implantable polymers which permit controlled release of polypeptide drugs are known, and can be used to prepare a botulinum toxin implant suitable for insertion or subdermal attachment. See e.g. Pain 1999;82(1):49–55; Biomaterials 1994;15(5):383–9; Brain Res 1990;515(1–2):309–11 and U.S. Pat. Nos. 6,022,554; 6,011,011; 6,007,843; 5,667,808, and; 5,980,945.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). Thus, an implant within the scope of the present invention can be surgically inserted by incision t the site of desired effect (i.e. for reduction of a muscle spasm) or the implant can be administered as a suspension, subcutaneously or intramuscularly using a hollow needle implanting gun, for example of the type disclosed in U.S. Pat. No. 4,474,572. The diameter of the needle may be adjusted to correspond to the size of the implant used. Further, an implant within the scope of the present invention can be implanted intracranially so as to provide long term delivery of a therapeutic amount of a neurotoxin to a target brain tissue. Removal of a non-biodegradable implant within the scope of the present invention is not essential once all neurotoxin has been released due to the biocompatible, nonimmunogenic nature of the implant materials used.

It is known that a significant water content of lyophilized tetanus toxoid can cause solid phase aggregation and inactivation of the toxoid once encapsulated within microspheres. Thus, with a 10% (grams of water per 100 grams of protein) tetanus toxoid water content about 25% of the toxin undergoes aggregation, while with a 5% water content only about 5% of the toxoid aggregates. See e.g. Pages 251, Schwendeman S. P. et al., *Peptide, Protein, and Vaccine Delivery From Implantable Polymeric Systems*, chapter 12 (pages 229–267) of Park K., Controlled Drug Delivery Challenges and Strategies, American Chemical Society (1997). Significantly, the manufacturing process for BOTOX® results in a freeze dried botulinum toxin type A complex which has a moisture content of less than about 3%, at which moisture level nominal solid phase aggregation can be expected.

A general procedure for making a pulsatile, biodegradable botulinum toxin implant is as follows. The implant can comprise from about 25% to about 100% of a polylactide which is a polymer of lactic acid alone. Increasing the amount of lactide in the implant can increases the period of time before which the implant begins to biodegrade, and hence increase the time to pulsatile release of the botulinum toxin from the implant. The implant can also be a copolymer of lactic acid and glycolic acid. The lactic acid can be either in racemic or in optically active form, and can be either soluble in benzene and having an inherent viscosity of from 0.093 (1 g. per 100 ml. in chloroform) to 0.5 (1 g. per 100 ml. in benzene), or insoluble in benzene and having an inherent viscosity of from 0.093 (1 g. per 100 ml in chloroform) to 4 (1 g. per 100 ml in chloroform or dioxin). The implant can also comprise from 0.001% to 50% of a botulinum toxin uniformly dispersed in carrier polymer.

Once implanted the implant begins to absorb water and exhibits two successive and generally distinct phases of neurotoxin release. In the first phase neurotoxin is released through by initial diffusion through aqueous neurotoxin regions which communicate with the exterior surface of the implant. The second phase occurs upon release of neurotoxin consequent to degradation of the biodegradable polymer (i.e. a polylactide). The diffusion phase and the degradation-induced phase are temporally distinct in time. When the implant is placed in an aqueous physiological environment, water diffuses into the polymeric matrix and is partitioned between neurotoxin and polylactide to form aqueous neurotoxin regions. The aqueous neurotoxin regions increase with increasing absorption of water, until the continuity of the aqueous neurotoxin regions reaches a sufficient level to communicate with the exterior surface of the implant. Thus, neurotoxin starts to be released from the implant by diffusion through aqueous polypeptide channels formed from the aqueous neurotoxin regions, while the second phase continues until substantially all of the remaining neurotoxin has been released.

Also within the scope of the present invention is an implant in the form of a suspension for use by injection, prepared by suspending the neurotoxin encapsulated microspheres in a suitable liquid, such as physiological saline.

EXAMPLES

The following examples set forth specific compositions and methods encompassed by the present invention and are not intended to limit the scope of the present invention.

Example 1

Method for Making a Biodegradable Botulinum Toxin Implant

A biodegradable implant comprising botulinum toxin and a suitable carrier polymer can be prepared by dispersing an appropriate amount of a stabilized botulinum toxin preparation (i.e. non-reconstituted BOTOX®) into a continuous phase consisting of a biodegradable polymer in a volatile organic solvent, such as dichloromethane. Both PLGA and polyanhydrides are insoluble in water and require use of organic solvents in the microencapsulation process.

The polymer is dissolved in an organic solvent such as methylene chloride or ethyl acetate to facilitate microsphere fabrication. The botulinum toxin is then mixed by homogenization or sonication to form a fine dispersion of toxin in polymer/organic solvent, as an emulsion when an aqueous protein solution is used or as a suspension when a solid protein formulation is mixed with the polymer-organic solvent solution. The conventional processes for microsphere formation are solvent evaporation and solvent (coacervation) methods. Microspheres can be formed by mixing the preformed suspension of protein drug with polymer-organic solvent, with water containing an emulsifier (i.e. polyvinyl alcohol). Additional water is then added to facilitate removal of the organic solvent from the microspheres allowing them to harden. The final microspheres are dried to produce a free flowing powder.

The polymer used can be PLA, PGA or a co-polymer thereof. Alternately, a botulinum toxin incorporating polymer can be prepared by emulsifying an aqueous solution of the neurotoxin (i.e. reconstituted BOTOX®) into the polymerorganic phase (obtaining thereby a W/O emulsion). With either process a high speed stirrer or ultrasound is used to ensure uniform toxin mixing with the polymer. Microparticles 1–50 μm in diameter can be formed by atomizing the emulsion into a stream of hot air, inducing the particle formation through evaporation of the solvent (spray-drying technique). Alternately, particle formation can be achieved by coacervation of the polymer through non-solvent addition, e.g. silicon oil (phase separation technique) or by preparing a W/O/W emulsion (double emulsion technique).

The pH of the casting or other solution in which the botulinum toxin is to be mixed is maintained at pH 4.2–6.8, because at pH above about pH 7 the stabilizing nontoxin proteins can dissociate from the botulinum toxin resulting in gradual loss of toxicity. Preferably, the pH is between about 5–6. Furthermore the temperature of the mixture/solution should not exceed about 35 degrees Celsius, because the toxin can be readily detoxified when in a solution/mixture heated above about 40 degrees Celsius.

Methods for freezing droplets to form microparticles include directing the droplets into or near a liquefied gas, such as liquid argon and liquid nitrogen to form frozen microdroplets which are then separated from the liquid gas. The frozen microdroplets can then be exposed to a liquid non-solvent, such as ethanol, or ethanol mixed with hexane or pentane.

A wide range of sizes of botulinum toxin implant microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. The size of the microparticles can be produced by this process, for example microparticles ranging from greater than about 1000 to about 1 micrometers in diameter.

Example 2

Method for Making a Polyanhydrides Botulinum Toxin Implant

A biodegradable polyanhydride polymer can be made as a copolymer of polycarboxyphenoxypropane and sebacic acid in a ratio of 20:80. Polymer and a botulinum toxin (such as non-reconstituted BOTOX®) can be co-dissolved in methylene chloride at room temperature and spray-dried into microspheres, using the technique of Example 1. Any remaining methylene chloride can be evaporated in a vacuum desiccator.

Depending upon the implant size desired and hence the amount of botulinum toxin, a suitable amount of the microspheres can be compressed at about 8000 p.s.i. for 5 seconds or at 3000 p.s.i. for 17 seconds in a mold to form implant discs encapsulating the neurotoxin. Thus, the microspheres can be compression molded pressed into discs 1.4 cm in diameter and 1.0 mm thick, packaged in aluminum foil pouches under nitrogen atmosphere and sterilized by $2.2 \times 10^4$ Gy gamma irradiation. The polymer permits release of the botulinum toxin over a prolonged period, and it can take more than a year for the polymer to be largely degraded.

Example 3

Water in Oil Method for Making a Biodegradable Botulinum Toxin Implant

A pulsatile release botulinum toxin implant can be made by dissolving a 80:20 copolymers of polyglycolic acid and the polylactic acid can in 10% w/v of dichloromethane at room temperature with gentle agitation. A water-in-oil type emulsion can then be made by adding 88 parts of the polymer solution to 1 part of a 1:5 mixture of Tween 80 (polyoxyethylene 20 sorbitan monooleate, available from Acros Organics N.V., Fairlawn, N.J.) and Span 85 (sorbitan trioleate) and 11 parts of an aqueous mixture of 75 units of BOTOX® (botulinum toxin type A complex) and Quil A (adjuvant). The mixture is agitated using a high-speed blender and then immediately spray-dried using a Drytec Compact Laboratory Spray Dryer equipped with a 60/100/120 nozzle at an atomizing pressure of 15 psi and an inlet temperature of 65 degrees C. The resultant microspheres have a diameter of about 20 µm diameter and are collected as a free-flowing powder. Traces of remaining organic solvent are removed by vacuum evaporation.

Example 4

Reduced Temperature Method for a Biodegradable Pulsatile Botulinum Toxin Implant A pulsatile release botulinum toxin delivery system can be made at a low temperature so as to inhibit toxin denaturation as follows. 0.3 g of PLGA/ml of methylene chloride or ethyl acetate is mixed with 0.1 ml of neurotoxin solution/ml of the polymer-organic solution at a reduced temperature (2–8 degrees C.). A first set of botulinum toxin incorporating microspheres made, as set forth in Example 1 (the polymer solution is formed by dissolving the polymer in methylene chloride), from a 75:25 lactide:glycolide polymer with an inherent viscosity (dL/g) of about 0.62 (available form MTI) can degrade in vivo, and hence exhibit a pulsed release of the botulinum toxin, at about ninety days post implantation and extending over 2–4 weeks. A second set of, botulinum toxin incorporating microspheres made, as previously set forth (the polymer solution is formed by dissolving the polymer in ethyl acetate), from a 100:0 lactide:glycolide polymer with an inherent viscosity of about 0.22 (available form MTI) can degrade in vivo, and hence exhibit a burst release of the botulinum toxin, at about one hundred and eighty days post implantation. A third set of, botulinum toxin incorporating microspheres made, as previously set forth (the polymer solution is formed by dissolving the polymer in methylene chloride, from a 95:5 poly(DL-lactide):glycolide polymer, can degrade in vivo, and hence exhibit a burst release of the botulinum toxin, at about two hindered and seventy days post implantation. A fourth set of botulinum toxin incorporating microspheres made, as previously set forth (the polymer solution is formed by dissolving the polymer in methylene chloride), from a 100:0 poly(DL-lactide):glycolide polymer can degrade in vivo, and hence exhibit a burst release of the botulinum toxin, at about twelve months post implantation. Polymers can be obtained from Medisorb Technologies International (MTI).

A suspension or compression molded pellet which combines the four specified sets of botulinum toxin encapsulated microspheres can exhibit pulsatile release the neurotoxin. Local administration of botulinum toxin at the time of implantation (i.e. day zero) is provided by the initial burst release from the implanted microspheres.

Compositions and methods according to the invention disclosed herein has many advantages, including the following:

1. a single implant can be used to provide therapeutically effective continuous or pulsatile administration of a neurotoxin over a period of one year or longer.
2. the neurotoxin is delivered to a localized tissue area without a significant amount of neurotoxin appearing systemically.
3. reduced need for patient follow up care.

4. reduced need for periodic injections of neurotoxin to treat a condition, such as a neuromuscular disorder.

5. increased patent comfort due to the reduced number of injections required.

6. improved patient compliance.

An advantage of the present controlled release formulations for neurotoxins include long term, consistent therapeutic levels of neurotoxin at the target tissue. The advantages also include increased patient compliance and acceptance by reducing the required number of injections.

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local (i.e. intramuscular, intraglandular, subcutaneous, and intracranial) administration methods wherein two or more neurotoxins, such as two or more botulinum toxins, are administered concurrently or consecutively via implant. For example, botulinum toxin type A can be administered via implant until a loss of clinical response or neutralizing antibodies develop, followed by administration via implant of a botulinum toxin type B or E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin via implant so as to provide an adjunct effect such as enhanced or a more rapid onset of denervation before the neurotoxin, such as a botulinum toxin, begins to exert its therapeutic effect.

The present invention also includes within its scope the use of a neurotoxin, such as a botulinum toxin, in the preparation of a medicament, such as a controlled release implant, for the treatment of a movement disorder, and/or a disorder influenced by cholinergic innervation, by local administration via the implant of the neurotoxin.

Accordingly, the spirit and scope of the following claims should not be limited to the descriptions of the preferred embodiments set forth above.

I claim:

1. A pulsatile release botulinum toxin delivery system, comprising:
   (a) a carrier;
   (b) a botulinum toxin associated with the carrier, thereby forming a pulsatile release botulinum toxin delivery system,
   wherein therapeutic amounts of the botulinum toxin can be released from the carrier in a plurality of pulses in vivo upon subdermal implantation of the delivery system in a human patient without a significant immune system response.

2. The delivery system of claim 1, wherein the carrier comprises a plurality of polymeric microspheres.

3. The delivery system of claim 1, wherein substantial amounts of the botulinum toxin has not be transformed into a botulinum toxoid prior to association of the botulinum toxin with the carrier.

4. The delivery system of claim 1, wherein significant amounts of the botulinum toxin associated with the carrier have a toxicity which is unchanged relative to the toxicity of the botulinum toxin prior to association of the botulinum toxin with the carrier.

5. The delivery system of claim 1, wherein the carrier comprises a polymeric matrix.

6. The delivery system of claim 1, wherein the botulinum toxin can be released from the carrier over of a period of time of from about 10 days to about 6 years.

7. The delivery system of claim 1, wherein the carrier is comprised of a substance which is biodegradable.

8. The delivery system of claim 1, wherein the botulinum toxin is selected from the group consisting of botulinum toxin types A, B, $C_1$, D, E, F and G.

9. The delivery system of claim 1, wherein the botulinum toxin is a botulinum toxin type A.

10. The delivery system of claim 1, wherein the quantity of the botulinum toxin associated with the carrier is between about 1 unit and about 50,000 units of the botulinum toxin.

11. The delivery system of claim 1, wherein the quantity of the botulinum toxin is between about 10 units and about 2,000 units of a botulinum toxin type A.

12. The delivery system of claim 1, wherein the quantity of the botulinum toxin is between about 100 units and about 30,000 units of a botulinum toxin type B.

13. A controlled release system, comprising:
   (a) a biodegradable polymer;
   (b) between about 10 units and about 100,000 units of a botulinum toxin encapsulated by the polymer carrier, thereby forming a controlled release system, wherein therapeutic amounts of the botulinum toxin can be released from the carrier in a pulsatile manner in vivo upon subdermal implantation of the controlled release system in a human patient over a prolonged period of time extending from about 2 months to about 5 years without a significant immune system response.

14. A method for making a controlled release system, the method comprising the steps of:
   (a) dissolving a polymer in a solvent to form a polymer solution;
   (b) mixing or dispersing a botulinum toxin in the polymer solution to form a polymer-botulinum toxin mixture, and;
   (c) allowing the polymer-botulinum toxin mixture to set or cure, thereby making a controlled release system for pulsatile release of the botulinum toxin without a significant immune system response.

15. The method of claim 14, further comprising the step after the mixing step of evaporating solvent.

16. A method for using a pulsatile drug delivery system, the method comprising injection or implantation of a controlled release system which includes a polymeric matrix and a botulinum toxin, thereby treating a movement disorder or a disorder influenced by cholinergic innervation by local administration of a botulinum toxin without a significant immune system response.

17. A pulsatile release botulinum toxin delivery system, comprising:
   (a) a carrier comprising a polymer selected from the group of polymers consisting of polylactides, polyglycolides and polyanhydrides, wherein the carrier further comprises a plurality of discrete sets of polymeric, botulinum toxin incorporating microspheres, each set of polymers having a different polymeric composition;
   (b) a stabilized botulinum toxin associated with the carrier, thereby forming a pulsatile release botulinum toxin delivery system,
   wherein the botulinum toxin comprises:

(a) a first element comprising a binding element able to specifically bind to a neuronal cell surface receptor under physiological conditions,
(b) a second element comprising a translocation element able to facilitate the transfer of a polypeptide across a neuronal cell membrane, and
(c) a third element comprising a therapeutic element able, when present in the cytoplasm of a neuron, to inhibit exocytosis of acetylcholine from the neuron, wherein the therapeutic element can cleave a soluble N-ethylmaleimide-sensitive factor attachment protein receptor (SNARE), thereby inhibiting the exocytosis of acetylcholine from the neuron, and, wherein therapeutic amounts of the botulinum toxin can be released from the carrier in a plurality of pulses in vivo upon subdermal implantation of the delivery system in a human patient without a significant immune system response.

18. The delivery system of claim 17, wherein the carrier comprises a plurality of discrete sets of polymeric, botulinum toxin incorporating microspheres, wherein each set of polymers has a different polymeric composition.

19. The delivery system of claim 18, wherein the SNARE is selected from the group consisting of syntaxin, a 25 kilo Dalton synaptosomal associated protein (SNAP-25) and a vesicle associated membrane protein (VAMP).

20. The delivery system of claim 18, wherein the neuron is a presynaptic, cholinergic, peripheral motor neuron.

* * * * *